United States Patent
Moszner et al.

(10) Patent No.: US 11,357,708 B2
(45) Date of Patent: Jun. 14, 2022

(54) DENTAL COMPOSITES WITH IMPROVED STORAGE STABILITY

(71) Applicant: Ivoclar Vivadent AG, Schaan (LI)

(72) Inventors: Norbert Moszner, Mauren (LI); Urs Karl Fischer, Arbon (CH); Ulrich S. Schubert, Jena (DE); Martin Hager, Jena (DE)

(73) Assignee: Ivoclar Vivadent AG, Schaan (LI)

( * ) Notice: Subject to any disclaimer, the term of this patent is extended or adjusted under 35 U.S.C. 154(b) by 524 days.

(21) Appl. No.: 15/541,257

(22) PCT Filed: Jan. 8, 2016

(86) PCT No.: PCT/EP2016/050286
§ 371 (c)(1),
(2) Date: Jul. 24, 2018

(87) PCT Pub. No.: WO2016/110571
PCT Pub. Date: Jul. 14, 2016

(65) Prior Publication Data
US 2018/0318178 A1    Nov. 8, 2018

(30) Foreign Application Priority Data
Jan. 9, 2015    (EP) ................................. 15150607

(51) Int. Cl.
*A61K 6/887* (2020.01)
*A61K 6/61* (2020.01)
*A61K 6/62* (2020.01)

(52) U.S. Cl.
CPC .............. *A61K 6/887* (2020.01); *A61K 6/61* (2020.01); *A61K 6/62* (2020.01)

(58) Field of Classification Search
CPC ....... A61K 6/083; A61K 6/0052; A61K 6/005
See application file for complete search history.

(56) References Cited

U.S. PATENT DOCUMENTS

| 5,773,194 A * | 6/1998 | Hattori | G03F 7/033 522/111 |
| 5,858,617 A * | 1/1999 | Nakayama | G03F 7/031 430/920 |
| 6,391,286 B1 * | 5/2002 | Mitra | A61K 6/0017 106/35 |
| 2004/0171728 A1 * | 9/2004 | Xue | C08L 51/10 524/420 |
| 2009/0047633 A1 * | 2/2009 | Huo | A61K 6/893 433/217.1 |
| 2011/0028589 A1 * | 2/2011 | Saimi | A61K 6/887 523/115 |
| 2013/0303655 A1 * | 11/2013 | Eckert | A61K 6/083 523/116 |

FOREIGN PATENT DOCUMENTS

JP    2013095690 A    5/2013
JP    2014214122 A    11/2014

OTHER PUBLICATIONS

Ikkai et al. (Mechanism of UV-Induced Gelation of Acryloyl-Type Monomer and Polymer Solutions Using Persulfate as Photoinitiator, Macromol. Chem. Phys. 2007, 208, 271-276) (Year: 2007).*
Ayres, Niel, "Atom Transfer Radical Polymerization: A Robust and Versatile Route for Polymer Synthesis," Polymer Reviews, 51:138-162, 2011,Taylor & Francis Group, LLC.
Kamigaito, M., et al., "Metal-Catalyzed Living Radical Polymerization," Chem. Rev. 2001, 101, 3689-3745, Dept. of Polymer Chemistry, Graduate School of Engineering, Kyoto University, Kyoto 606-8501, Japan.
Jakubowski, W., et al., "Activators Regenerated by Electron Transfer for Atom-Transfer Radical Polymerization of (Meth)acrylates and Related Block Copolymers," Angew. Chem. 2006, 118, 4594-4598, Wiley-VCH Verlag GmbH & Co. KGaA, Weinheim.
Tasdelen, M. et al., "Visible Light-Induced Atom Transfer Radical Polymerization," Macromolecular Chemistry and Physics, 2012, 2013, 1391-1396, Wiley, VCH Verlag GmbH & Co. KGaA, Weinham.
Matyjaszewski, K. et al., "Diminishing catalyst concentration in atom transfer radical polymerization with reducing agents," PNAS, Oct. 17, 2006, vol. 103, No. 42, 15309-15314, Department of Chemistry, Carnegie Mellon University, Pittsburgh, Pennsylvania.
International Preliminary Report on Patentability of PCT/EP2016/050286, dated Jul. 11, 2017, 8 pages.

* cited by examiner

*Primary Examiner* — Jessica M Roswell
(74) *Attorney, Agent, or Firm* — Ann M. Knab; Thad McMurray

(57) ABSTRACT

Dental material which contains (a) at least one mono- or multifunctional radically polymerizable monomer, (b) at least one organic halogen compound as initiator for the radical polymerization, (c) at least one transition metal compound as catalyst and (d) at least one reducing agent. The material is characterized by a high storage stability at room temperature and does not have the disadvantages associated with peroxides.

18 Claims, No Drawings

DENTAL COMPOSITES WITH IMPROVED STORAGE STABILITY

CROSS-REFERENCE TO RELATED APPLICATIONS

This application is a National Stage application of International patent application PCT/EP2016/050286 filed on Jan. 8, 2016, which claims priority to European patent application No. 15150607.8 filed on Jan. 9, 2015, the disclosures of which are incorporated herein by reference in their entirety.

FIELD OF THE INVENTION

The present invention relates to redox-chemically or dual-curing composites for the preparation of dental materials such as dental cements for fixing crowns, bridges, inlays or onlays, and filling materials.

BACKGROUND OF THE INVENTION

Dental composites, which are used e.g. as composite cement or as direct filling material, inlay, onlay, crown or veneering material, contain a polymerizable organic matrix and one or more fillers, which are usually surface-modified with a polymerizable adhesion promoter. Depending on the type of fillers, the monomer matrix and the desired application, the fill level can vary between approx. 50-90 wt.-%, wherein cements have a lower fill level compared with filling composites.

The present invention relates to redox-chemically or dual-curing composites for the preparation of dental materials such as dental cements for fixing crowns, bridges, inlays or onlays, and filling materials.

Dental composites, which are used e.g. as composite cement or as direct filling material, inlay, onlay, crown or veneering material, contain a polymerizable organic matrix and one or more fillers, which are usually surface-modified with a polymerizable adhesion promoter. Depending on the type of fillers, the monomer matrix and the desired application, the fill level can vary between approx. 50-90 wt.-%, wherein cements have a lower fill level compared with filling composites.

As a rule, the polymerizable organic matrix contains a mixture of monomers, initiator components, stabilizers and pigments. Mixtures of dimethacrylates are usually used as monomers. Examples of these are the highly viscous dimethacrylates 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) as well as the dimethacrylates of lower viscosity used as diluting monomers, such as e.g. bismethacryloyloxymethyltricyclo[5.2.1.]decane (TCDMA), decanediol-1,10-dimethacrylate ($D_3MA$) and triethylene glycol dimethacrylate (TEGDMA).

Various radical-forming initiators are used in the curing of dental composites based on dimethacrylates. Light-curing composites often contain camphorquinone (CQ) as photoinitiator, which absorbs light in the blue range of the visible spectrum (400-500 nm). To accelerate the light-induced disintegration of the CQ, tertiary amines such as e.g. EMBO (4-dimethylaminobenzoic acid ethyl ester) are used as coinitiators, from which polymerization-initiating aminoalkyl radicals form.

Besides photoinitiators, redox-chemically curing initiator systems which consist of an oxidizing agent, usually a peroxide such as dibenzoyl peroxide (DBPO), and a reducing agent are commonly used. Tertiary aromatic amines such as N,N-diethanol-p-toluidine or N,N-diethyl-3,5-di-tert.-butylaniline have proved to be worthwhile as reducing agent. These reducing agents accelerate the radical-forming decomposition of the DBPO with the result that polymerization can be initiated at room temperature. In composites which contain acid monomers, amine-free redox systems are preferred because acids lead to the neutralization of the basic amine accelerator. Amine-free reducing agents which are suitable for combining with peroxides and hydroperoxides are e.g. ascorbic acid, p-toluene sulphinic acid and trimethyl barbituric acid.

Redox systems are always used when, as e.g. in the case of fixing composites, light initiation cannot be used due to a lack of sufficient light transmission. The curing takes place significantly more slowly in comparison with light curing. Fixing composites often also contain so-called dual-curing initiator systems. As a rule this is a combination of a photoinitiator and a redox initiator system.

Peroxides have a severely limited thermal stability and can explode spontaneously in the presence of impurities. In order to be able to use them in practice nevertheless, so-called phlegmatizing agents such as e.g. phthalates are added for stabilization, which, however, can lead to toxicological problems. Peroxide redox initiator systems and in particular the DBPO redox systems often used in dental materials have the further disadvantage that they have only a limited storage stability and must therefore be refrigerated during storage and transportation.

The so-called atom transfer radical polymerization (ATRP) does not require peroxides. Here, a combination of transition metal complexes, above all copper, ruthenium or iron complexes, with organohalogen compounds is used to initiate the radical polymerization (N. Ayres, Polym. Rev. 51 (2011) 138-162; T. Ando, M. Kamigaito, M. Sawamoto, Macromolecules, 2000, 33, 5825-5829). A disadvantage of ATRP is that relatively large amounts of metal are necessary and that the metal catalysts are easily oxidized. The required transition metal concentration can be reduced by adding reducing agents, such as e.g. tin(II)-2-ethylhexanoate or glucose (W. Jakubowski, K. Matyjazewski, Angew. Chem. 118 (2006) 45). By adding certain photoinitiators such as bis-(2,4,6-trimethylbenzoxyl)phenylphosphine oxide or certain dyes such as Eosin Y and Erythrosin B, the ATRP can also be directly or indirectly induced by light (M. A. Tasdelen, M. Ciftci, Y. Yagci, Macromol. Chem. Phys. 213 (2012) 1391-1396).

ATRP is a multicomponent system which, in addition to the monomer, contains an initiator with a transferable halogen group and a catalyst which is composed of a transition metal and suitable ligands. The primary aim of ATRP is to achieve a controlled radical polymerization, i.e. control of the molecular weight and the achievement of a narrow molecular weight distribution. Since it is not possible to control the molecular weight in the case of cross-linking polymerization, because it increases rapidly to infinite numbers due to the cross-linking, to date practically exclusively non-crosslinking monomers, i.e. monomers with only one radically polymerizable group, have been investigated. Dental materials which can be cured by means of ATRP are not known.

SUMMARY OF THE INVENTION

The object of the invention is to provide dental materials and in particular dental composites which are characterized in comparison with known materials based on dimethacrylates by an improved storage stability at room temperature, which contain no phlegmatizing agent and which cure rapidly by redox-chemical means.

DETAILED DESCRIPTION

The object is achieved according to the invention by dental materials which contain
(a) at least one mono- or multifunctional radically polymerizable monomer, preferably a mono- or multifunctional methacrylate,
(b) at least one organic halogen compound,
(c) at least one transition metal compound,
(d) at least one reducing agent and
(e) preferably at least one filler.

The dental materials according to the invention contain as component (a) at least one radically polymerizable monomer, preferably a mixture of radically polymerizable monomers, in particular one or more (meth)acrylates, particularly preferably a mixture of mono- and polyfunctional methacrylates, quite particularly preferably of mono- and difunctional methacrylates. Those dental materials are preferred which contain as radically polymerizable monomers exclusively mono- and or polyfunctional methacrylates. By monofunctional monomers is meant compounds with one, by polyfunctional monomers compounds with two or more, preferably 2 to 4, radically polymerizable groups.

Preferred mono- or polyfunctional methacrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A dimethacrylate, bis-GMA (an addition product of methacrylic acid and bisphenol A diglycidyl ether), ethoxylated or propoxylated bisphenol A dimethacrylate, such as e.g. the bisphenol A dimethacrylate SR-348c with 3 ethoxy groups or 2,2-bis[4-(2-methacryloxypropoxy)phenyl]propane, UDMA (an addition product of 2-hydroxyethyl methacrylate (HEMA) and 2,2,4-trimethylhexa-methylene diisocyanate), TMX-UDMA (an addition product of a mixture of HEMA and hydroxypropyl methacrylate (HPMA) with α,α,α',α'-tetramethyl-m-xylylene diisocyanate (TMXDI), di-, tri- or tetraethylene glycol dimethacrylate, trimethylolpropane trimethacrylate, pentaerythritol tetramethacrylate, as well as glycerol di- and trimethacrylate, 1,4-butanediol dimethacrylate, 1,10-decanediol dimethacrylate ($D_3MA$) or 1,12-dodecanediol dimethacrylate. Particularly suitable are mixtures of CMP-1E, UDMA, and TMX-UDMA as well as glycerol di- or glycerol trimethacrylate and/or $D_3$-MA.

According to the invention, a monomer mixture is preferably used which contains at least one low-volatile monomethacrylate, at least one highly viscous poly-, preferably difunctional methacrylate and at least one low-viscosity poly-, preferably difunctional methacrylate.

According to the invention, by low-volatile monomers is meant compounds with a boiling point >150° C. at normal pressure. The boiling point can e.g. be determined using a distillation apparatus. By highly viscous monomers is meant substances with a viscosity ≥5 Pa·s, preferably 5 to 10,000 Pa·s and particularly preferably 5 to 2,000 Pa·s, and by low-viscosity monomers is meant substances with a viscosity 300 mPa·s, preferably 1 to 300 mPa·s and particularly preferably 30 to 300 mPa·s, wherein the viscosity is determined using a capillary viscometer (low-viscosity) or rotational viscometer (highly viscous) at a temperature of 25° C.

Particularly preferred highly viscous dimethacrylates are TMX-UDMA (an addition product of HEMA and hydroxypropyl methacrylate (HPMA) with α,α,α',α'-tetramethyl-m-xylylene diisocyanate (TMXDI)) and 1,6-bis-[2-methacryloyloxyethoxycarbonylamino]-2,4,4-trimethylhexane (UDMA). Preferred low-viscosity dimethacrylates which are used as diluting monomers are bismethacryloyloxymethyltricyclo-[5.2.1.]decane (TCDMA), glycerol dimethacrylate (GDMA) and in particular decanediol-1,10 dimethacrylate ($D_3MA$). A particularly preferred low-volatile monomethacrylate is p-cumylphenoxyethylene glycol methacrylate (CMP-1E).

The organic halogen compound (b) functions as initiator for the atom transfer radical polymerization (ATRP). It has at least one transferable halogen atom and forms radicals during the reaction with the transition metal complex (c) through the transfer of the halogen atom to the metal complex. The transition metal complex (c) acts as catalyst.

Preferred organic halogen compounds (b) are:

Halogenated alkyl aromatics, such as e.g. benzyl halides, in particular benzyl chloride or bromide, 1-phenylethyl chloride, benzotrichloride and benzhydryl chloride or bromide.

α-Halogen carboxylic acid esters, in particular $C_1$-$C_6$-alkyl esters of an α-halogen-$C_1$-$C_6$-carboxylic acid, such as α-chloropropionic acid, α-bromopropionic acid, α-chloro-iso-butanoic acid, α-bromo-iso-butanoic acid, α-bromophenylacetic acid. Particularly preferred are esters of the α-bromo-iso-butanoic acid such as α-bromo-isobutanoic acid methyl and ethyl ester, α-bromoisobutyryl bromide, 2-(2-bromoisobutyryl-oxy)ethyl methacrylate, tert-butyl α-bromoisobutyrate or 3-butynyl-2-bromoisobutyrate, dipentaerythritol hexakis(2-bromoisobutyrate) or 1,1,1-tris(2-bromoisobutyryloxy-methyl)ethane or ethyl α-bromophenylacetate.

α-Halogenketones, such as e.g. 1,1,1-trichloro-propan-2-one or dichloromethyl phenyl ketone.

α-Halogen nitriles, such as e.g. 2-bromopropionitrile or trichloroacetonitrile.

Sulphonyl halides, methyl-, trichloromethyl-, p-toluene- or 4-methoxyphenylsulphonyl chloride.

Halogen compounds which contain chlorine or bromine as transferable halogen atoms are preferred.

As transition metal compound (c) transition metal complex compounds are preferred, in particular transition metal complex compounds of the metals copper, iron, ruthenium, nickel and palladium. Instead of the transition metal complexes, non-complex salts of the transition metals in combination with complex-forming organic compounds can be used for the preparation of dental materials. On mixing with the transition metal salts, the organic ligands form the catalytically active complexes. The use of such combinations of transition metal salts and organic ligands is preferred.

P- and in particular N-containing ligands are preferred as complexing organic compounds. Preferred examples for this are phosphines, preferably triphenylphosphine; ethylenediaminetetraacetic acid (EDTA); phenanthrolines, preferably 1,10-phenanthroline (Phen); bipyridines, preferably 2,2'-bipyridine (Bipy), 4,4'-dimethyl-2,2'-bipyridine, 6,6'-dimethyl-2,2'-bipyridine and 4,4'-di(5-nonyl)-2,2'-bipyridine (dNbpy); terpyridines, preferably 2':6',2''-terpyridine (tpy), 4,4',4''-tris(5-nonyl)-2,2':6',2''-terpyridine; pyridinimines, preferably N-octyl-2-pyridylmethanimine; alkylated imidazoles, preferably 1,3-diisopropyl-4,5-dimethylimidazol-2-ylidene (PriIm); alkylamino-substituted benzenes, preferably o,o'$(CH_2NMe_2)_2C_6H_3$; aliphatic amines, preferably 1,1,4,7,10,10-hexamethyltriethylenetetramine (HMTETA), N,N,N',N'',N''-penta-methyldiethylenetriamine (PMDETA), tris[2-(dimethylamino)-ethyl]amine (Me$_6$TREN), N,N,N', N'-tetramethylethylenediamine (TMEDA), 1,4,8,11-tetraaza-1,4,8,11-tetramethylcyclo-tetradecane (Me4CYCLAM), diethylenetriamine (DETA), triethylenetetramine (TETA) and 1,4,8,11-tetraazacyclotetradecane (CYCLAM)); pyridine-containing ligands, preferably N,N,N', N'-tetrakis(2-pyridylmethyl)ethylenediamine (TPEN), N,N-bis(2-pyridylme-thyl)amine (BPMA) and N,N-bis(2-pyridylmethyl)octylamine (BPMOA), alkyl-substituted 2-(1H-1,2,3-triazol-4-yl)pyridines, 2,6-bis(1H-1,2,3-triazol-4-yl)-pyridine and alkyl-substituted 2,6-bis(1H-1,2,3-triazol-4-yl)pyridines.

Preferred copper salts are CuCl, CuBr, CuCl$_2$, CuBr$_2$, CuI$_2$, Cu(II) carboxylates (e.g. of acetic acid or 2-ethylhexanoic acid). Preferred copper complexes are complexes with the ligands phenanthroline (e.g. 1,10-phenanthroline (Phen)), terpyridine, bipyridine (e.g. 2,2'-bipyridine (Bipy), 4,4'-dimethyl-2,2'-bipyridine or 6,6'-dimethyl-2,2'-bipyridine), pyridinimine or aliphatic amines, such as e.g. 1,1,4,7,10,10-hexamethyltriethylenetetramine (HMTETA), N,N,N',N'',N''-penta-methyldiethylenetriamine (PMDETA), tris[2-(dimethylamino)ethyl]amine (Me$_6$TREN).

Preferred iron salts are FeCl$_3$, FeBr$_2$ and FeCl$_2$. Preferred iron complexes are complexes with the ligands triphenylphosphine, 4,4'-di(5-nonyl)-2,2'-bipyridine (dNbpy) or 1,3-diisopropyl-4,5-dimethylimidazol-2-ylidene (PriIm). Quite particularly preferably the complexes are FeCl$_2$(PPh$_3$)$_2$, FeBr$_2$-dNbpy, FeCl$_2$(PriIm)$_2$ and FeBr$_2$(PriIm)$_2$.

A preferred ruthenium salt is RuCl$_2$, preferred ruthenium complexes are RuCl$_2$(PPh$_3$)$_4$ and RuH$_2$(PPh$_3$)$_4$.

Preferred nickel salts are NiBr$_2$ and NiCl$_2$, preferred nickel complexes are Ni[o,o'(CH$_2$NMe$_2$)$_2$C$_6$H$_3$]Br and NiBr$_2$(PPh$_3$)$_2$.

A preferred palladium salt is Pd(OAc)$_2$.

In all cases, those complexes are preferred in which the respective transition metal is present in its most stable oxidation state. Complexes of Cu$^{2+}$, Fe$^{3+}$, Ni$^{2+}$, Ru$^{3+}$ and Pd$^{2+}$ are therefore preferred.

According to the invention, copper compounds, copper complexes and in particular mixtures of copper salts and complexing organic ligands are particularly preferred.

When using a combination of non-complex transition metal salt and complexing organic compound, the transition metal salt and ligand are preferably used in a molar ratio of 1:1 to 1:100, particularly preferably 1:5 to 1:100. The complexes required for initiating the polymerization form in situ on mixing transition metal salt and ligand.

Preferred reducing agents (d) are tin compounds, such as Sn(II) octoate or Sn(II)-2-ethylhexanoate, reducing sugars, e.g. glucose or fructose, antioxidants, such as e.g. ascorbic acid (vitamin C) and derivatives thereof (preferred derivatives of ascorbic acid are salts and esters thereof), β-carotenoids (preferably vitamin A), α-tocopherol (vitamin E), phenolic reducing agents, such as e.g. butylhydroxytoluene (BHT), butylhydroxyanisole (BHA), propyl or octyl gallate, pyrogallol, sulphites, bisulphites, thiosulphates, hydroxylamine and hydrazine as well as derivatives of hydroxylamine and of hydrazine, i.e. in particular N-substitution products of hydroxylamine and of hydrazine, or a combination of different reducing agents. Sn(II) compounds and ascorbic acid as well as esters and salts thereof are particularly preferred.

The dental materials according to the invention are preferably present in the form of composites. By composites is meant compositions which, in addition to the above-named constituents, contain at least one organic or preferably inorganic filler (constituent e).

Particularly suitable are fillers based on oxides with a particle size of from 0.01 to 15 µm, such as SiO$_2$, ZrO$_2$ and TiO$_2$ or mixed oxides of SiO$_2$, ZrO$_2$, ZnO and/or TiO$_2$; nanoparticulate fillers with a particle size of from 5 to 300 nm, preferably 10 to 300 nm, such as pyrogenic silica or precipitated silica; as well as glass powders with a particle size of from 0.01 to 15 µm, preferably from 0.2 to 1.5 µm, such as quartz, glass ceramic or X-ray opaque glass powders of e.g. barium or strontium aluminium silicate glasses; and X-ray opaque fillers with a particle size of from 0.2 to 5 µm, such as ytterbium trifluoride, tantalum(V) oxide, barium sulphate or mixed oxides of SiO$_2$ with ytterbium(III) oxide or tantalum(V) oxide. Fibrous fillers, nanofibres or whiskers are not excluded, particulate fillers are preferred, however. Unless otherwise stated, all particle sizes are weight-average particle sizes.

The fillers are also divided, according to particle size, into macrofillers and microfillers. Here, by macrofillers is meant fillers with a particle size of from 0.5 µm to 15 µm and by microfillers is meant fillers with a particle size of from 5 to 300 nm. The dental materials according to the invention preferably contain a mixture of macro- and microfillers. Macrofillers with an average particle size of from 0.5 to 10 µm are preferred. The microfillers preferably have an average particle size of from 5 to 100 nm.

Macrofillers are obtained by grinding, for example, quartz, X-ray opaque glasses, borosilicates or from ceramic, are preferably of a purely inorganic nature and mostly consist of splinter-like particles. Pyrogenic SiO$_2$ or precipitated silica are preferably used as microfillers, or also mixed oxides, e.g. SiO$_2$—ZrO$_2$, which can be obtained by hydrolytic cocondensation of metal alkoxides.

In addition, so-called composite fillers can be used as macrofillers. These are particulate, for example splinter-like, microfilled polymers, which can be obtained e.g. by incorporating pyrogenic SiO$_2$ and/or X-ray opaque glass fillers into a resin matrix, subsequent thermal polymerization of the mixture and grinding of the polymer thus obtained. Composite fillers are also called isofillers.

To improve the bond between the filler particles and the cross-linked polymerization matrix, SiO$_2$-based fillers can be surface-modified with (meth)acrylate-functionalized silanes. A preferred example of such silanes is 3-(meth)acryloyl-oxypropyltrimethoxysilane. To surface-modify non-silicate fillers, such as e.g. ZrO$_2$ or TiO$_2$, functionalized acid phosphates, such as e.g. 10-(meth)acryloyloxydecyl dihydrogen phosphate can also be used.

The fill level is geared to the desired intended use. Filling composites preferably have a filler content of from 75-90 wt.-% and composite cements preferably from 40-75 wt.-%, preferably 50 to 60 wt.-%.

According to a preferred embodiment the dental materials preferably contain in addition as constituent (f) at least one photoinitiator for the radical polymerization. Dual-curing materials can be obtained by adding a photoinitiator, wherein α-diketones, such as 9,10-phenanthrenquinone, 1-phenyl-propane-1,2-dione, diacetyl or 4,4'-dichlorobenzil are preferred as photoinitiators. Particularly preferably camphorquinone (CQ) and 2,2-dimethoxy-2-phenyl-acetophenone and quite particularly preferably α-diketones in each case in combination with an amine, such as e.g. 4-(dimethylamino)-benzoic acid ester (EMBO), N,N-dimethylaminoethyl methacrylate, N,N-dimethyl-sym.-xylidine or triethanolamine are used as reducing agent. Further preferred are Norrish Type I photoinitiators, above all acyl- or bisacylphosphine oxides, and in particular monoacyl trialkyl and diacyl dialkyl germanium compounds, such as e.g. benzoyltrimethylgermanium, dibenzoyldiethylgermanium or bis (4-methoxybenzoyl)diethylgermanium (MBDEGe). Mixtures of these photoinitiators are also suitable, such as e.g. bis(4-methoxybenzoyl)diethylgermanium in combination with CQ/EMBO. Dual-curing materials are particularly suitable as fixing cements.

In addition, the compositions according to the invention can contain further additives (constituent g), above all stabilizers, dyes, microbiocidal active ingredients, fluoride-ion-releasing additives, propellants, optical brighteners and/or UV absorbers. Aerobic stabilizers, e.g. phenols such as BHT or MEHQ (hydroquinone monomethyl ether), and anaerobic stabilizers, such as phenothiazine or N,N'-diphenyl-1,4-phenylenediamine, are particularly suitable as stabilizers.

The materials according to the invention contain no peroxides and preferably also no plasticizers and/or phlegmatizing agents, i.e. in particular no phthalates. Furthermore it is preferred that the materials according to the invention contain no acid monomers. In all embodiments, the materials according to the invention are preferably free from solvent.

The dental materials according to the invention preferably contain:
(a) 5 to 80 wt.-%, preferably 10 to 70 wt.-% and particularly preferably 15 to 60 wt.-% mono- and/or multifunctional (meth)acrylate(s),
(b) 0.1 to 6.0 wt.-%, preferably 0.2 to 4.0 wt.-% and particularly preferably 0.2 to 3.0 wt.-% of at least one organic halogen compound,
(c) 0.0001 to 1.0 wt.-%, preferably 0.001 to 1.0 wt.-% and particularly preferably 0.001 to 0.1 wt.-% of at least one transition metal compound,
(d) 0.01 to 5.0 wt.-%, preferably 0.01 to 3.0 wt.-% and particularly preferably 0.1 to 2.0 wt.-% reducing agent and
(e) 10 to 85 wt.-%, preferably 22 to 82 wt.-% and particularly preferably 35 to 80 wt.-% filler(s).

Materials are particularly preferred which in addition contain
(f) 0.01 to 3.0 wt.-%, preferably 0.05 to 2.0 wt.-% and particularly preferably 0.1 to 1.0 wt.-% photoinitiator, and/or
(g) 0.001 to 5.0 wt.-%, preferably 0.001 to 3.0 wt.-% and particularly preferably 0.01 to 1.0 wt.-% additive(s).

If a non-complex transition metal salt is used as constituent (c), the compositions preferably contain additionally 0.0001 to 1.0 wt.-%, preferably 0.001 to 1.0 wt.-% and particularly preferably 0.01 to 1.0 wt.-% of at least one complexing organic compound.

Unless otherwise stated, all quantities relate to the total mass of the materials. The individual quantity ranges can be chosen separately.

Those dental materials that consist of the named components are particularly preferred. Furthermore, those materials are preferred in which the individual components are in each case selected from the above-named preferred and particularly preferred substances.

The materials according to the invention are characterized in that they can be cured redox-chemically but do not contain any peroxides and preferably also do not contain any plasticizers or phlegmatizing agents and therefore do not have the disadvantages associated with these substances. Moreover, they have a high storage stability at room temperature.

The compositions according to the invention can be cured redox-chemically or, if a photoinitiator is present, redox-chemically and by light (photochemically). The materials are preferably present in the form of at least 2, preferably 2, separate components which are mixed with each other for use. These components predominantly have the form of pastes. The individual constituents of the initiator system are distributed between the different components in such a way that the active initiator system is obtained and the polymerization is initiated only when the components are mixed. The transition metal compound (c) is preferably contained in a first component or paste and the halogen compound (c) and the reducing agent (d) are preferably contained in a second component or paste. I.e., the first paste preferably contains the constituents (a), (c), (e) and optionally one or more of the constituents (f)-(g) and the second component contains constituents (a), (b), (d), (e) and optionally one or more of the constituents (f)-(g). When the transition metal salt and ligand are used separately both constituents can be contained in the first component or paste or, according to another embodiment, the first component contains the transition metal salt and the second component additionally contains the ligand. For use, the pastes are thoroughly mixed with each other. The compositions of the individual components or pastes are calculated such that, after mixing, materials with the composition indicated above are obtained. According to the invention those materials are particularly preferred which can be cured under oral conditions (i.e. at approx. 37° C.)

The dental materials according to the invention are particularly suitable as dental cements and filling materials. They have very good storage stability and nevertheless cure rapidly, above all in comparison with the known dibenzoyl peroxide-containing dental materials, and do not contain any peroxides and preferably also do not contain any phlegmatizing agents, i.e. in particular no phthalates.

The dental materials are suitable primarily for intraoral application by the dentist to restore damaged teeth (clinical materials), e.g. as dental cements, dental filling materials and dental veneering materials. However, they can also be used extraorally, for example in the manufacture or repair of dental restorations, such as inlays, onlays, crowns and bridges (technical materials).

The invention is described in further detail in the following with reference to examples.

EMBODIMENT EXAMPLES

Example 1

Curing Tests of Curing Systems According to the Invention
To investigate the reactivity of the redox systems, different curing tests were investigated with a redox system according to the invention of BrBuE (α-bromoisobutyric acid ester; organic halide), CuEH (copper(II)-ethylhexanoate; transition metal compound), PMDETA (N,N,N',N'',N''-pentamethyldiethylene-triamine; ligand) and SnEH (tin(II)-ethylhexanoate) or AS6P (ascorbic acid 6-palmitate; reducing agent). For this, 10 g batches were prepared in jars with snap-on lids at room temperature after evacuating the air (desiccator in diaphragm pump vacuum). 1,4-Butanediol dimethacrylate (BDDMA) or triethylene glycol dimethacrylate (TEGDMA) were used as monomers (Table 1, values in mass-%). CuEH was in each case only added as last reaction component. A strongly exothermic polymerization took place in the reaction times indicated.

TABLE 1

Curing tests

| Monomer | BDDMA | TEGDMA | TEGDMA |
|---|---|---|---|
| Monomer content (%) | 97.63 | 97.13 | 97.60 |
| CuEH (%) | 0.04 | 0.004 | 0.0004 |
| BrBuE (%) | 1.35 | 1.46 | 1.40 |
| PMDETA (%) | 0.52 | 0.47 | 0.49 |
| SnEH | 0.47 | — | — |
| AS6P (%) | — | 0.47 | 0.47 |
| Time to start of reaction (min.) | 15 | 7 | 10 |

Example 2

Composite with Redox Initiator System According to the Invention

Using a mixer (SpeedMixer® DAC 150.1 FVZ; Hauschild, Germany), 3 min. at 2500 revolutions/min., 2 composite pastes with the composition indicated in Table 2 were prepared.

TABLE 2

Composition of the pastes

| Constituent | Paste A [wt.-%] | Paste B [wt.-%] |
|---|---|---|
| TEGDMA | 17.58 | 17.19 |
| Bis-GMA | 17.58 | 17.19 |
| CuEH | 0.30 | — |
| BrBuE | — | 0.48 |
| PMDETA | — | 0.17 |
| AS6P | — | 0.17 |
| $SiO_2$[1] | 44.50 | 44.80 |
| $YbF_3$[2] | 20.04 | 20.00 |
| Total | 100.0 | 100.00 |

[1] silanized pyrogenic silicia, primary particle size 40 nm (OX-50, Degussa)
[2] ytterbium trifluoride, average particle size 0.8 μm After mixing the pastes in the ratio 1:1 test pieces were prepared from the materials according to ISO 4049, which were cured for 4 h at 80° C. According to ISO standard 4049 (Dentistry-Polymer-based filling, restorative and luting materials), the bending strength was determined as 93 MPa and the flexural modulus of elasticity was determined as 5,700 MPa.

Example 3

Preparation of a Composite with Dual-Curing Initiator System

With a mixer (Speedmixer DAC 150.1 FVZ; Hauschild, Germany), 2 composite pastes with the composition indicated in Table 3 were prepared.

TABLE 3

Composition of the dual-curing composite

| Constituent | Paste A [wt.-%] | Paste B [wt.-%] |
|---|---|---|
| TEGDMA | 17.33 | 17.33 |
| Bis-GMA | 17.32 | 17.32 |
| CuEH | 346 ppm | — |
| BrBuE | 0.46 | 0.48 |
| PMDETA | — | 0.29 |
| AS6P | — | 0.69 |
| $SiO_2$[1] | 44.50 | 44.58 |
| $YbF_3$[2] | 19.79 | 17.79 |
| Camphorquinone | 0.21 | — |
| EMBO[3] | 0.36 | — |
| Total | 100.0 | 100.00 |

[1] silanized pyrogenic silicia, primary particle size 40 nm (OX-50, Degussa)
[2] ytterbium trifluoride, average particle size 0.8 μm
[3] 4-(dimethylamino) benzole acid ethyl ester After mixing the pastes in the ratio 1:1 test pieces were prepared from the materials which were first cured for 24 h at 37° C. and then for 2×3 min. in a light furnace (Spectramat; Ivoclar Vivadent AG). The curing at 37° C. started after 270 s (processing range), the curing time was 320 s. The measured mechanical properties are indicated in Table 4. The dimensions of the test pieces, the curing time, the processing time, the bending strength and the flexural modulus of elasticity were determined according to ISO standard 4049 (Dentistry-Polymer-based filling, restorative and luting materials).

TABLE 4

Mechanical properties of the dual-curing composite

| | Bending strength (MPa) | Flexural modulus of elasticity (GPa) |
|---|---|---|
| 37° C.[1] | 53.1 | 2.31 |
| 2 × 3 min. light furnace | 103.3 | 6.72 |

[1] Measurement took place according to ISO 4049 after 24-hour storage at 37° C.

The results show that it is possible to improve the mechanical properties significantly by combining an ATRP initiator system with a photoinitiator system.

The invention claimed is:
1. Dental material comprising
   (a) a mixture of at least one mono- and at least one polyfunctional methacrylate as radically polymerizable monomer,
   (b) at least one organic halogen compound,
   (c) at least one transition metal compound, and
   (d) at least one reducing agent,
   wherein said dental material does not comprise peroxides or solvents, wherein the transition metal compound is a compound of copper, iron, ruthenium, nickel or palladium and wherein the at least one halogen compound (b) is selected from halogenated alkyl aromatics, benzyl halides, benzyl chloride, benzyl bromide, 1-phenylethyl chloride, benzotrichloride, benzhydryl chloride, benzhydryl bromide; α-halogen carboxylic acid esters, $C_1$-$C_6$-alkyl esters of an α-halogen-$C_1$-$C_6$-carboxylic acid, α-chloropropionic acid, α-bromopropionic acid, α-chloro-isobutanoic acid, α-bromo-iso-butanoic acid, α-bromophenylacetic acid, esters of α-bromo-isobutanoic acid, α-bromo-isobutanoic acid methylester, α-bromo-isobutanoic acid ethylester, α-bromo-iso-butyryl bromide, 2-(2-bromoisobutyryloxy)ethyl methacrylate, tert-butyl α-bromoisobutyrate, 3-butynyl-2-bromo-iso-butyrate, dipentaerythritol hexakis(2-bromoisobutyrate), 1,1,1-tris(2-bromoisobutyryloxymethyl)ethane, ethyl α-bromophenylacetate; α-halogenketones, 1,1,1- trichloropropan-2-one, dichloromethyl phenyl ketone; α-halogen nitriles, 2-bromopropionitrile, trichloroacetonitrile; sulphonyl halides, methylsulphonyl chloride, trichloromethylsulphonyl chloride, p-toluenesulphonyl chloride and 4-methoxyphenylsulphonyl chloride.

2. Dental material according to claim 1 further comprising at least one organic and/or inorganic filler as constituent (e).

3. Dental material according to claim 1 comprising as monomer (a) a mixture of mono- and difunctional methacrylates.

4. Dental material according to claim 1 comprising as component (c) at least one transition metal complex compound which is selected from the complexes of the metals copper, iron, ruthenium, nickel and palladium; copper complexes with the ligands phenanthroline, 1,10-phenanthroline (Phen), terpyridine, bipyridine, 2,2'-bipyridine (Bipy), 4,4'-dimethyl-2,2'-bipyridine, 6,6'-dimethyl-2,2'-bipyridine, pyridinimine, aliphatic amines, 1,1,4,7,10,10-hexamethyltriethylenetetramine (HMTETA), N,N,N',N'',N''-pentamethyldiethylenetriamine (PMDETA) and tris[2-(dimethylamino)ethyl]amine ($Me_6TREN$); iron complexes with the ligands triphenylphosphine, 4,4'-di(5-nonyl)-2,2'-bipyridine (dNbpy) or 1,3-diisopropyl-4,5-dimethylimidazol-2-ylidene (PriIm), $FeCl_2(PPh_3)_2$, $FeBR_2$-dNbpy (dNbpy: 4,4'-di(5-nonyl)-2,2'-bipyridine), $FeC_2(PriIm)_2$ and $FeBr_2(PriIm)_2$ (PriIm: 1,3-diisopropyl-4,5-dimethylimidazol-2-ylidene); the ruthenium complexes $RuCl_2(PPh_3)_4$ and $RuH_2(PPh_3)_4$; or the nickel complexes $Ni[o,o'(CH_2NMe_2)C_6H_3]Br$ and $NiBr_2(PPh_3)_2$.

5. Dental material comprising
(a) a mixture of at least one mono- and at least one polyfunctional methacrylate as radically polymerizable monomer,
(b) at least one organic halogen compound,
(c) at least one transition metal compound, and
(d) at least one reducing agent,
wherein said dental material does not comprise peroxides or solvents, wherein the at least one transition metal compound is a
transition metal salt which is selected from the salts of the metals copper, iron, ruthenium, nickel and palladium, CuCl, CuBr, $CuCl_2$, $CuBr_2$, $CuI_2$, Cu(II) carboxylates, Cu(II) acetate, Cu(II)-2-ethylhexanoate, $FeCl_3$, $FeBr_2$, $FeCl_2$, $RuCl_2$, $NiBr_2$, $NiCl_2$, $Pd(OAc)_2$ and wherein the dental material additionally comprises at least one
complexing organic compound which is selected from P- and N-containing ligands, phosphines, triphenylphosphine; ethylenediaminetetraacetic acid (EDTA); phenanthrolines, 1,10-phenanthroline (Phen); bipyridines, 2,2'-bipyridine (Bipy), 4,4'-dimethyl-2,2'-bipyridine, 6,6'-dimethyl-2,2'-bipyridine and 4,4'-di(5-nonyl)-2,2'-bipyridine (dNbpy); terpyridines, 2':6',2''-terpyridine (tpy), 4,4',4''-tris(5-nonyl)-2,2':6',2''-terpyridine; pyridinimines, N-octyl-2-pyridylmethanimine; alkylated imidazoles, 1,3-diisopropyl-4,5-dimethylimidazol-2-ylidene (PriIm); alkylamino-substituted benzenes, $o,o'(CH_2NMe_2)_2C_6H_3$; aliphatic amines, 1,1,4,7,10,10-hexamethyltriethylenetetramine (HMTETA), N,N,N',N'',N''-pentamethyldiethylenetriamine (PMDETA), tris[2-(dimethylamino)ethyl]amine ($Me_6TREN$), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM)); pyridine-containing ligands, N,N,N',N'-tetrakis(2-pyridylmethyl)ethylenediamine (TPEN), N,N-bis(2-pyridylmethyl)amine (BPMA) and N,N-bis(2-pyridylmethyl)octylamine (BPMOA), alkyl-substituted 2-(1H-1,2,3-triazol-4-yl)pyridines, 2,6-bis(1H-1,2,3-triazol-4-yl)-pyridine and alkyl-substituted 2,6-bis(1H-1,2,3-triazol-4-yl)pyridines.

6. Dental material according to claim 1 comprising as reducing agent (d) at least one compound which is selected from ascorbic acid and derivatives thereof, tin compounds, Sn(II) octoate, Sn(II)-2-ethylhexanoate, reducing sugars, glucose, fructose, antioxidants, β-carotenoids, vitamin A, α-tocopherol (vitamin E), phenolic reducing agents, butylhydroxytoluene (BHT), butylhydroxyanisole (BHA), propyl gallate, octyl gallate, pyrogallol, sulphites, bisulphites, thiosulphates, hydroxylamine, hydrazine and derivatives thereof.

7. Dental material according to claim 1 further comprising a photoinitiator.

8. Dental material according to claim 1 comprising no plasticizers/phlegmatizing agents.

9. Dental material comprising
(a) 5 to 80 wt.-% of a mixture of at least one mono- and at least one polyfunctional methacrylate as radically polymerizable monomer,
(b) 0.1 to 6.0 wt.-% of at least one organic halogen compound,
(c) 0.0001 to 1.0 wt.-% of at least one transition metal compound,
(d) 0.01 to 5.0 wt.-% of at least one reducing agent and
(e) 10 to 85 wt.-% filler(s),
wherein said dental material does not comprise peroxides or solvents, wherein the transition metal compound is a compound of copper, iron, ruthenium, nickel or palladium and wherein, if constituent (c) is a non-complex transition metal salt, then the dental material additionally contains 0.0001 to 1.0 wt.-% of at least one complexing organic compound.

10. Dental material according to claim 9, which additionally comprises
(f) 0.01 to 3.0 wt.-% photoinitiator, and/or
(g) 0.001 to 5.0 wt.-% additive(s).

11. Dental material according to claim 10 which is present in the form of at least two separate components which are mixed with each other before use.

12. Dental material according to claim 11 which comprises a first component and a second component, wherein the first component contains the constituents (a), (c) and optionally one or more of the constituents (f)-(g) and the second component contains the constituents (a), (b), (d), (e) and optionally one or more of the constituents (f)-(g).

13. Dental material according to claim 1 for use as cement or filling material.

14. Dental material according to claim 1 manufactured into dental restorations, inlays, onlays, crowns or bridges.

15. Dental material according to claim 9 comprising
(a) 10 to 70 wt.-% mono- and polyfunctional (meth)acrylates,
(b) 0.2 to 4.0 wt.-% of at least one organic halogen compound,
(c) 0.001 to 1.0 wt.-% of at least one transition metal compound,
(d) 0.01 to 3.0 wt.-% reducing agent and
(e) 22 to 82 wt.-% filler(s),
wherein, if constituent (c) is a non-complex transition metal salt, then the dental material additionally contains 0.001 to 1.0 wt.-% of at least one complexing organic compound.

16. Dental material according to claim 9 comprising
(a) 15 to 60 wt.-% mono- and polyfunctional (meth)acrylates,
(b) 0.2 to 3.0 wt.-% of at least one organic halogen compound,
(c) 0.001 to 0.1 wt.-% of at least one transition metal compound,
(d) 0.1 to 2.0 wt.-% reducing agent and
(e) 35 to 80 wt.-% filler(s),
wherein, if constituent (c) is a non-complex transition metal salt, then the dental material additionally contains 0.01 to 1.0 wt.-% of at least one complexing organic compound.

17. Dental material according to claim 15, which additionally comprises
(f) 0.05 to 2.0 wt.-% photoinitiator, and/or
(g) 0.001 to 3.0 wt.-% additive(s).

18. Dental material according to claim 16, which additionally comprises
(f) 0.1 to 1.0 wt.-% photoinitiator, and/or
(g) 0.01 to 1.0 wt.-% additive(s).

\* \* \* \* \*